(12) United States Patent
Drake, Jr.

(10) Patent No.: US 6,571,633 B1
(45) Date of Patent: Jun. 3, 2003

(54) REMOTE LASER BEAM DELIVERY SYSTEM AND METHOD FOR USE WITH A GANTRY POSITIONING SYSTEM FOR ULTRASONIC TESTING PURPOSES

(75) Inventor: Thomas E. Drake, Jr., Fort Worth, TX (US)

(73) Assignee: Lockheed Martin Corporation, Bethesda, MD (US)

( * ) Notice: Subject to any disclaimer, the term of this patent is extended or adjusted under 35 U.S.C. 154(b) by 97 days.

(21) Appl. No.: 09/766,085

(22) Filed: Jan. 19, 2001

(51) Int. Cl.[7] .................. G01N 29/06; G01N 29/26
(52) U.S. Cl. .................. 73/621; 73/620; 73/643; 73/655; 73/634
(58) Field of Search .................. 73/643, 655, 656, 73/657, 618, 619, 620, 621, 627, 634, 633; 356/2

(56) References Cited

U.S. PATENT DOCUMENTS

| | | | |
|---|---|---|---|
| 5,672,830 A | * | 9/1997 | Rogers et al. .................. 73/597 |
| 5,698,787 A | * | 12/1997 | Parzuchowski et al. ........ 73/583 |
| 6,285,514 B1 | * | 9/2001 | O'Meara et al. ............. 359/577 |
| 6,378,387 B1 | * | 4/2002 | Froom ........................ 73/865.8 |

* cited by examiner

Primary Examiner—Hezron Williams
Assistant Examiner—Rose M. Miller
(74) Attorney, Agent, or Firm—Hughes & Luce LLP

(57) ABSTRACT

A system and method for delivering a laser beam from a remote laser source through a gantry positioning system for performing ultrasonic testing on a test object. The invention provides for closed-loop error correction of a laser beam delivered through the gantry members of a gantry positioning system (GPS) to ensure unobstructed transmission of the laser beam as the GPS changes operates and changes shape. The invention provides for ultrasonic testing of a test object for identifying material defects by moving the end gantry member of the GPS thereby permitting data acquisition of the test object from various fields of view. The invention also provides for controlling the divergence of the laser beam used for ultrasonic testing.

20 Claims, 2 Drawing Sheets

REMOTE LASER BEAM DELIVERY SYSTEM AND METHOD FOR USE WITH A GANTRY POSITIONING SYSTEM FOR ULTRASONIC TESTING PURPOSES

TECHNICAL FIELD OF THE INVENTION

The present invention relates generally to a system and method for guiding a beam of light through the orthogonal axes of a mechanical positioning system for directing the beam at an object for ultrasonic testing, and more particularly, to a system and method for delivering a laser beam generated by a remote laser source through a gantry positioning system for use in detecting material defects of a test object using ultrasonic techniques.

BACKGROUND INFORMATION

It is desirable for a variety of applications to provide for mechanically directing a laser beam to any location within a predetermined volume. Many of these applications are tailored specifically for use within industrial manufacturing applications employing automated, robotics systems. Over the past several decades, the advent of robotics and laser light source technologies have led to many integrated systems for assembly line manufacturing . For example, robotics assembly systems incorporating laser technologies are very typical in automobile and even aircraft manufacturing plants for performing such tasks as welding.

For many systems, a robotic or gantry positioning system having a mechanical armature is often used to direct a laser beam to a variety of locations of a single workpiece. This armature itself provides for precision directing of the laser beam from the end of the mechanical armature. A laser beam delivery system is normally integrated into the gantry positioning system (GPS), particularly into the mechanical armature, for directing the laser beam from the end of the mechanical armature to any location within a predetermined volume. Specifically, the laser beam is then directed to portions of a workpiece and often from various fields of view for welding, cutting, ablating, or any variety of applications employing a laser beam. While the concept of incorporating a laser beam delivery system into a mechanical armature system for delivering to a workpiece is known to those skilled in the art, the methods and manners for accomplishing this goal may be very diverse.

Various technologies employ a method or system for directing a laser beam through a robotics system, e.g. U.S. Pat. No. 4,661,680 "End-of-arm tooling carousel apparatus for use with a robot" by R. L. Swensrud; U.S. Pat. No. 4,659,902 "Robot laser system" by R. L. Swensrud et al.; U.S. Pat. No. 4,539,462 "Robotic laser beam, delivery apparatus" by D. J. Plankenhorn. These technologies generally employ a plurality of tubular members, optically coupled to one another, through which a laser beam passes for directing the laser beam from the end of a GPS or "orthogonal axis manipulator system" (See Swensrud U.S. Pat. No. 4,659,902). These optical components for directing the laser beam through the laser beam delivery system may include spherical joint lenses or precision aligned mirrors at the pivotal connections of the armature of the GPS.

For GPSs that are relatively small in size and whose mechanical armature is light in weight, the directing of the laser beam through the armature may be provided by using a number of mirrors that are permanently located in fixed positions at the junctures of the mechanical armature. However, larger GPSs may include large carriage assemblies common to industrial workshops and other similar settings. The mechanical members of the GPS may bend and stress significantly depending on the position of the carriage assembly and the shape of the mechanical armature. These bends and stresses may result in laser beam steering within the segments of the GPS and ultimately may result in obstruction of the laser beam altogether. This stems from the fact that the mirrors are firmly attached to the mechanical armature of the GPS, and as the shape of the GPS bends, the mirrors: may come out of alignment. A common solution for this problem in those laser beam delivery systems that employ air cavity propagation of the laser beam in enclosed segments along the axes of the GPS is to require significantly large dimensioned enclosed segments to accommodate the substantial bending associated with a large GPS while maintaining a large working envelope. Additionally, larger mirrors may be required to accommodate and correct for this beam steering to ensure unobstructed transmission of the laser beam. This requirement may substantially increase the size of the laser beam delivery system within the GPS. This may also increase the cost for materials required for the laser beam delivery system as well as further complicate the integration of the laser beam delivery system into the GPS given its larger bulk.

Small GPSs may not suffer from such problems as severe bending and stresses given their relatively small size, yet the intrinsic different needs of various sized GPSs makes utilizing a single laser beam delivery system in variety of different sized GPSs extremely difficult. GPSs which are relatively small in size and light in weight do not require large members and mirrors through which a laser beam propagates; large GPSs require either a large working enveloped through which the laser beam travels or some additional modification to accommodate the bending of the mechanical armature of the GPS to maintain unobstructed laser beam propagation. However, some lasers suffer from beam pointing instabilities. This requires corrective alignment procedures to maintain long-term operation when employing long distance free space beam delivery methods. An approach for providing laser beam delivery through a gantry positioning system that is scaleable and adaptable to a variety of sizes and shapes of GPSs irrespective of the overall size and weight of the armatures of the GPS is desirable.

While a large GPS may comprise a laser beam delivery system with large members through which a laser beam propagates to overcome the problems of beam obstruction resulting from bending and stressing of the GPS as it changes shape, as described above, many problems remain in that the laser beam delivery system must be designed specifically for the GPS in question. The larger the size and heavier the weight of the GPS, the more beam steering may occur resulting in possible beam obstruction requiring larger members and mirrors to ensure unobstructed beam transmission. Such a solution to beam obstruction requires the size of the members through which a laser beam propagates be tailored specifically to the size, weight, and operating constraints of GPS in question.

Ultrasonic testing is a method which may be used to detect material defects in a objects comprised of various materials. A common application for ultrasonic testing is to detect inhomogeneities in composite materials. Ultrasonic testing may be used to serve a variety of industrial needs including identification of defects in manufactured goods for tuning of manufacturing processes. Manufacturers of products comprising composite material may wish to identify imperfections in their articles of manufacture to modify their manufacturing process to strive for greater repeatability and efficiency in their process or simply to identity problem areas within their process. Composite materials comprise many critical components within modern, high performance aircraft, and are becoming more common in terrestrial applications such as the automotive industry. Composite materials are desirable for many of their inherent attributes including light weight, high strength, and stiffness. Particularly for aircraft application, those composite material components, which may be large and complex in shape, are often flight critical necessitating strict assurance of material and structural integrity.

Unfortunately, these materials are sometimes fabricated with imperfections or develop them after several hours of use. These material defects may appear as a delamination of the surface of the material, porosity, an inclusion, debonds between bonded sub-components, or a void within the component itself. This inhomogeneity in the structure severely weakens it, providing a situation which might result in catastrophic failure. A conventional method for detecting material defects in a composite material utilizes piezoelectric transducers in conjunction with mechanical scanners mounted across the surface of the composite to detect any material imperfections. The disadvantages of the conventional methods are many, including difficulty in accommodating non-flat or evenly mildly contoured composite materials. Another disadvantage is the requirement that the transducer couple to the material via a water path. The transducer must remain normal to the surface within ±3° during a scan. To accommodate highly-contoured and complex shaped components using conventional techniques often requires extremely time-intensive test set up preparation.

Laser ultrasonic testing is an alternative method that is used to identify these imperfections. For aircraft applications, particularly for military fighter aircraft, all flight critical parts fabricated of composite material must be fully inspected before installation. A GPS comprising a laser beam delivery system may be integrated with a laser ultrasonic testing system for providing automated identification of material defects of a test object.

One approach is to mount the laser ultrasonic testing system comprising a laser source on the end of the mechanical armature of the GPS. The use of a GPS allows the ultrasonic testing system to be maneuvered around the test object to provide for positioning the laser source in close proximity to the test object from a multitude of locations of fields of vision. For those ultrasonic testing systems which use high power gas lasers such as $CO_2$ lasers, the large and bulky size of the laser complicates the integration of the ultrasonic testing system with the GPS as the end segment of the mechanical armature must be capable of supporting a significantly heavy weight at its end. The large size and bulky weight of the light source itself often demands the use of a very large GPS capable of supporting the heavy weight of an ultrasonic testing system as it is maneuvered around the test object to perform data acquisition from a variety of perspectives.

The conventional method of incorporating a GPS with an ultrasonic testing system cannot provide for the interfacing of data acquisition of the test object after the laser beam has been delivered to it from a remote location, aside from mounting the entire ultrasonic testing system on the end segment of the mechanical armature wherein only the laser source is located remotely. To overcome the requirement of a large and robust GPS to be used for ultrasonic testing of a test object for identifying material defects, a system or method is required which will not only provide for the delivery of a laser beam from a remote laser source, but also perform data acquisition of the test object from a remote location. Though the art provides for the combination of a GPS with a laser beam delivery system for the delivery of a laser beam to a workpiece, there is no teaching or suggestion for the integration of a GPS with an ultrasonic testing system which comprises a laser source and data acquisition system which is operated remotely from the workpiece as well as the end of the mechanical armature of the GPS.

SUMMARY OF THE INVENTION

The present invention utilizes a robotic or gantry positioning system (GPS) with an integral laser beam delivery system for delivering a laser beam from a remote laser source to a test object for detecting material defects using a laser ultrasonic testing system. The gantry positioning system may have the form of any variety of positioning systems commonly known to those skilled in the art. A typical configuration will generally include a mechanical armature that allows for the placement of its end to any location within a desired work space. This armature commonly includes a number of straight segments connected at each end and is operated using a number of actuators which provide for the moving and directing of the armature throughout the work space for some desirable or useful purpose. This GPS may take the form of a relatively small robotic-type armature; it may take the form of a system resembling an industrial crane common to machine shops and other industrial facilities; it may take the form of any number of configurations of various sizes and weights which provide for the movement of the end of a mechanical armature throughout the entirety of a defined work space.

The present invention includes a laser beam delivery system which is integrated into the GPS for transmitting a laser beam along the axes of motion of the GPS while its mechanical armature is in operation. The axes of motion of the GPS often correspond to the gantry members of the mechanical armature which combine to form the GPS; the gantry members are often connected in some pivotal manner to allow for freedom of movement in multiple directions. The laser beam is delivered through the entire GPS to a test object for performing ultrasonic testing on the test object. Each of the gantry members of the mechanical armature of the GPS comprises an optical transmission channel to guide the laser beam after being injected into the first gantry member of the GPS.

Additionally, the present invention provides a number of alignment fixtures within these optical transmission channels and a position feedback sensor to detect whether or not the laser beam is transmitting through the entire GPS free from obstruction. This position feedback sensor emits an alignment signal indicating whether or not the laser beam is transmitting fully through the alignment fixtures. The GPS allows the laser beam to be directed from the end segment of the mechanical armature at the test object from multiple points of view, thereby providing ultrasonic testing from all encompassing perspectives of the test object. For complete analysis of the test object, the GPS provides for ultrasonic testing of the object from a first field of view, then normally from several additional fields of view. Data from each of these fields of view is then utilized for detecting any material defects of the test object using ultrasonic techniques.

When using laser ultrasonic techniques, it is desirable to use a laser source of high output power to provide sufficient heat and excitation of the material of the test object. A typical laser source for use in ultrasonic testing is a carbon dioxide gas laser ($CO_2$ gas laser). However, those skilled in the art will recognize a number of other lasers may also be used. A number of mirrors also assist to direct and guide the laser beam from the optical transmission channels of the various gantry members of the GPS. At least one mirror is located at the each of the connection points of the mechanical armature of the GPS to guide it from the optical transmission channels of adjacent gantry members. The angular alignment mirrors in the present invention is controlled by a number of mirror actuators which adjust the angular alignment of the mirrors in response to the alignment signals from the above-mentioned position feedback sensors. If the laser beam has somehow become obstructed and no longer transmits through the GPS, the mirror actuators change the angular alignment of the mirrors to re-align the path of the laser beam until transmission is re-established. Such a system and method provides for closed-loop error correction in real time to ensure transmission of the laser beam through the entire GPS.

Laser beam divergence is an additional problem that may occur in a system which provides for the directing of a laser beam, particularly where the medium of the system is air. For the present invention, a laser beam conditioning system comprises part of the laser beam delivery system for minimizing the divergence of the laser beam as it propagates through the GPS as well as providing for the conditioning of the beam to maintain certain properties after the laser beam has exited the GPS. Laser light diverges as it propagates due to its intrinsic Gaussian nature. Those skilled in the art recognize many different methods of minimizing the Gaussian beam divergence of a free space propagating laser beam.

A very common approach is to position a lens, or a sequence of lenses at predetermined locations along the propagation path of the laser beam to reshape the beam as it propagates to maintain the desired properties of the beam along the entire propagation path. For example, in the present invention, lenses could be placed along the optical transmission channels of the gantry segments at various locations that are calculated to maintain the same properties of the laser beam at entrance and exit of the GPS. The lenses may also be located near the mirrors which guide the laser beam from the optical transmission channels of the various gantry members of the GPS. Bulk optical lenses are not the only components of which the laser beam conditioning system provides may be comprised. Those skilled in the art can readily envision a number of additional components which may be used to minimize divergence of a propagating beam, such a various apertures, gratings, crystals, etc., which may all cooperate to minimize the divergence of the laser beam as it propagates through the GPS. Laser beam divergence may also present a problem after the laser beam has exited the end gantry member. The user of the present invention may wish to focus the laser beam on a specific location of the test object. A laser beam conditioning system provides the user with great flexibility to control various laser beam properties during transmission through the GPS as well as after the beam has left the GPS entirely.

The present invention employs a laser ultrasonic testing system which is used to identify and detect material defects in a test object. Data is acquired of the test object and is analyzed for identifying any material defects in the test object and for providing the precise locations of them. Identifying material defects in composite materials, particularly those within aircraft applications, may provide aircraft designers with information concerning actual life and fatigue of flight critical, composite components as well as provide manufacturers of composite components with information concerning stress and failure points of the component. The ultrasonic testing system within this invention is provided and presented in detail in U.S. patent application Ser. No. 09/343,920 entitled "System and Method for Laser Ultrasonic Testing" by T. E. Drake, Jr.

The present invention provides an important technical advantage by providing a laser beam delivery system which is scaleable and adaptable to a variety of gantry positioning systems (GPSs) of varying sizes and weight by providing closed-loop error correction of the transmission of a laser beam provided by a remote laser source through a GPS.

The present invention provides another technical advantage by providing for automated data acquisition of a test object by moving the end gantry member of a GPS around the test object in between various acquisitions of data thereby providing multiple fields of view of the test object for ultrasonic testing purposes.

The present invention provides another technical advantage by providing for focusing of the laser beam by using a laser beam conditioning system. This laser beam conditioning system permits the user of the present invention to control various properties of the laser beam that is used for ultrasonic testing purposes.

BRIEF DESCRIPTION OF THE DRAWINGS

For a more complete understanding of the present invention and the advantages thereof, reference is now made to the following description taken in conjunction with the accompanying drawings in which like reference numerals indicate like features and wherein.

DETAILED DESCRIPTION OF THE INVENTION

Preferred embodiments of the present invention are illustrated in the FIGURES, like numerals being used to refer to like and corresponding parts of the various drawings.

The present invention employs a gantry positioning system with an integral laser beam delivery system for delivering a laser beam delivered by a remote laser source to a test object for performing ultrasonic testing to detect any material defects in the test object. The gantry positioning system provides for scanning the entire test object from various fields of view to map out the test object using laser ultrasonic techniques. Data are recorded from all of the fields of view and later processed to provide for not only the detection of any such material defects, but also their location within the test object.

Figure 1:
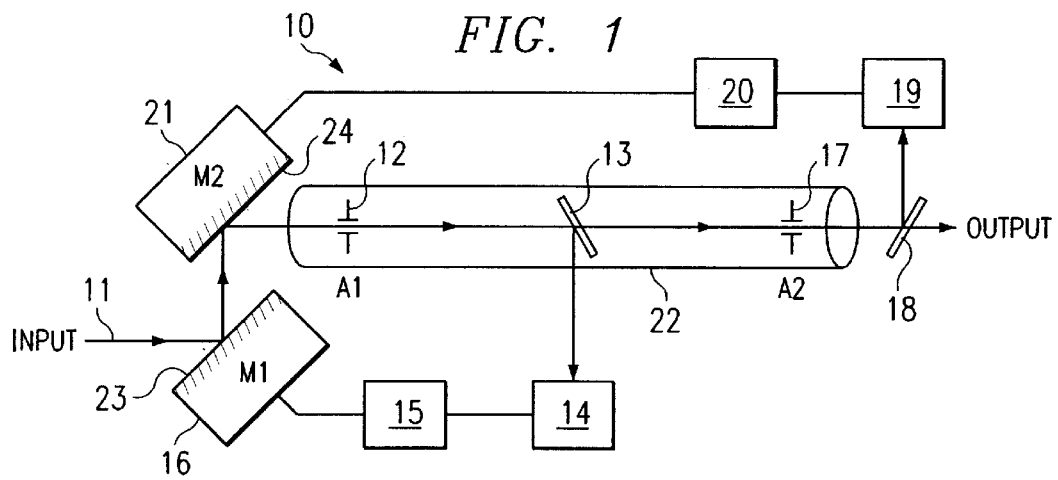
FIG. 1 shows a laser guiding configuration for transmitting a laser beam through two alignment apertures.

FIG. 1 shows a system 10 for providing closed loop feedback for directing a laser beam 11 through a first alignment aperture 12 and a second alignment aperture 17 contained within an optical transmission channel 22. A laser beam 11 is reflected off of a first dual axis mirror 23 which provides for angular alignment and directing to a second dual axis mirror 24 for subsequent directing through the alignment apertures 12 and 17.

A beam splitter or diffractive sampling element 13 takes a portion of the laser beam and directs it to a detector 14 comprising an optical detector. An output signal from the position sensitive detector 14 is then fed to a logic circuit 15 which determines whether or not the laser beam 11 has passed through the first alignment aperture 12. If the laser beam 11 has not passed through the first alignment aperture 12, then a signal is sent from the logic circuit 15 to adjust to angular alignment of the first dual axis mirror 23 using a first mirror actuator 16. Such a system provides for closed-loop error correction of the laser beam through the GPS.

An analogous procedure is performed with respect to the second alignment aperture 17, except with the adjusting of the second dual axis mirror 24 using a second mirror actuator 21. A beam splitter 18 directs a portion of the laser beam 11 to a position sensitive detector 19, which then provides an output signal to a logic circuit 20 for providing closed-loop error correction of the second dual axis mirror 24 using a second mirror actuator 21. If detectors 14 and 19 are position sensitive detectors, then apertures 12 and 17 can be omitted and the error signal is derived from 14 and 19 only.

Figure 2:
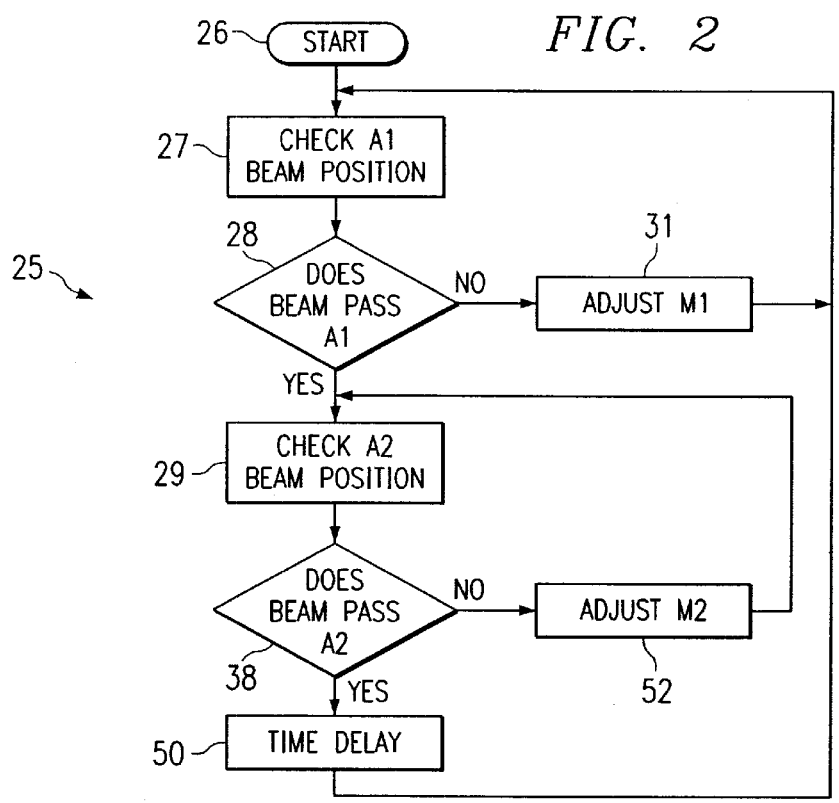
FIG. 2 shows the mirror adjusting algorithm for transmitting a laser beam through two alignment apertures used by the configuration of FIG. 1.

FIG. 2 shows the algorithm in flowchart format 25 which the system of FIG. 1 employs. In operation, the first step 26 shows the start of a measurement procedure. Step 27 depicts the next step of checking the A1 beam position. If, as step 28 tests, the laser beam passes point A1, a next check of the A2 beam position occurs at step 29. If the beam does not pass point A1, then mirror M1 is adjusted at step 31. Step 38 performs a test of whether the beam passes point A2. If so, process flow goes to time delay step 50 and then back to step 27 for checking the A1 beam position. If the laser beam does not pass A2, mirror M2 is adjusted at step 52 and process flow then goes to step 29 to, again, check the beam position at point A2.

Figure 3:
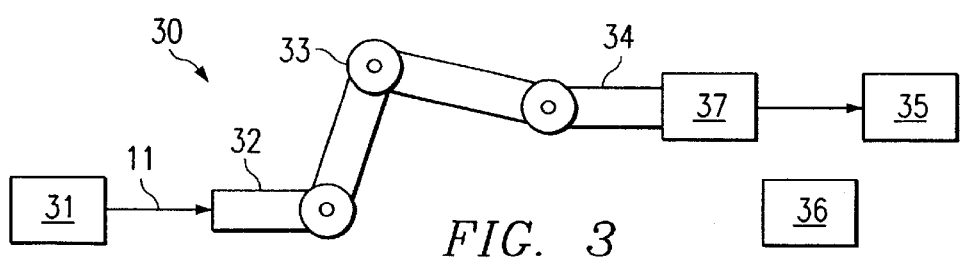
FIG. 3 shows one embodiment of a gantry positioning and ultrasonic testing system with an integral laser beam delivery system.

FIG. 3 shows one embodiment 30 of a gantry positioning and ultrasonic testing system with an integral laser beam delivery system. A laser beam 11 is generated by a remote laser source 31 and inserted into the optical transmission channel of a first gantry member 32. Each gantry member of the gantry positioning system comprises an optical alignment system similar to that described in FIG. 2 for guiding the laser beam 11 through the gantry positioning system and for delivering it to a test object 35 for performing ultrasonic testing. The gantry positioning system is comprised of a number of gantry members pivotally connected. At each of these pivotal connections is a gantry actuator 33 for controlling the shape of the gantry positioning system which provides for positioning the end gantry member 34 to any location within the desired workspace in which the test object 35 is located. By permitting the gantry positioning system to be manipulated around the workspace of the test object 35 allows for performing ultrasonic testing using an ultrasonic testing system 36 from a variety of fields of view. Additionally, a laser beam conditioning system 37 may be used to provide for minimizing the divergence of the laser beam 11 as it exits the end gantry member 34 of the gantry positioning system and is delivered to the test object 35. The laser beam conditioning system 37 could likewise be included within the optical transmission channels 22 of the gantry segments of the GPS to provide for conditioning and minimizing the divergence of the beam as it propagates through the GPS.

Figure 4:
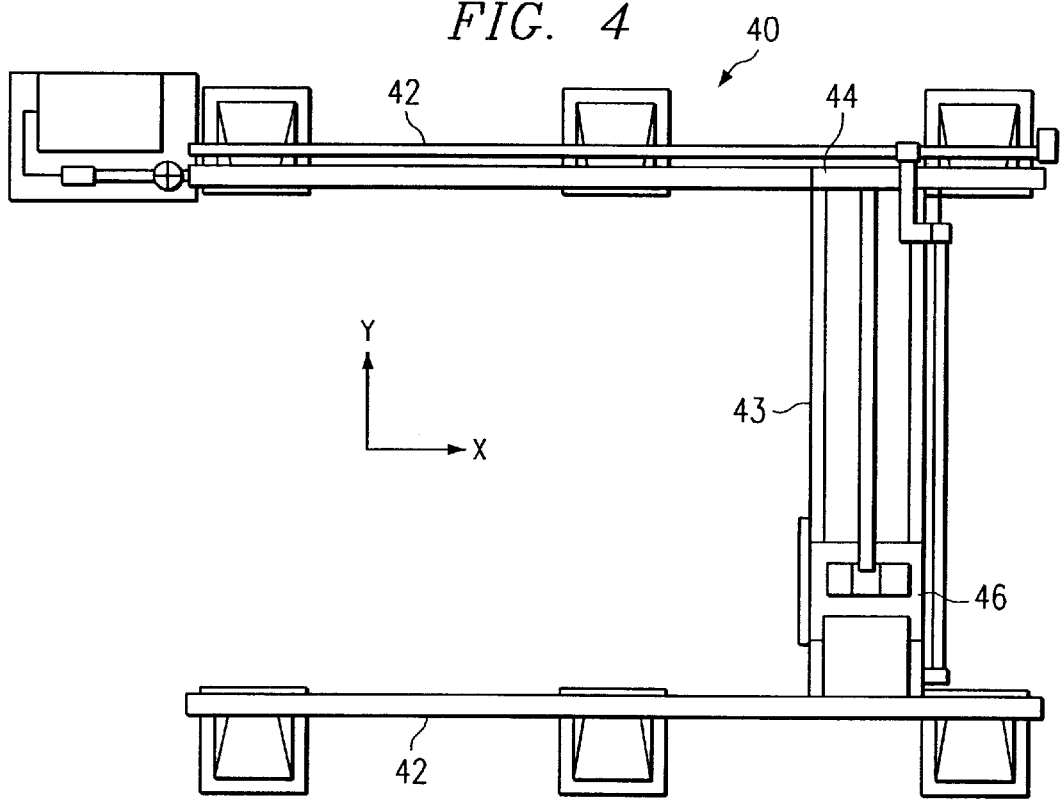
FIG. 4 shows a particular embodiment of FIG. 3 of gantry positioning and ultrasonic testing system with an integral laser beam delivery system.
Figure 5:
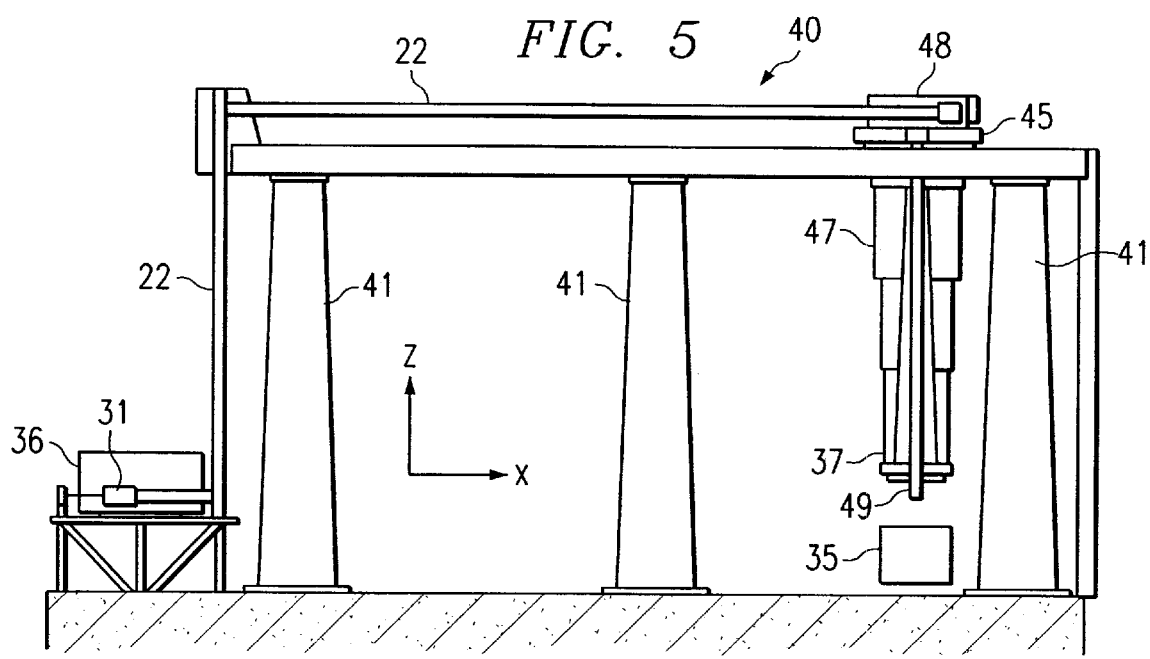
FIG. 5 depicts an embodiment of the present invention.

FIG. 4 shows a particular embodiment 40 of FIG. 3 of a gantry positioning and ultrasonic testing system with an integral laser beam delivery system. The gantry positioning system is comprised of a plurality of vertical supports beams 41 which support two runway beams 42 which run parallel to one another. A bridge beam 43 spans between the two runway beams and is powered using a bridge beam actuator 44 for providing translation in a first direction, depicted as the X direction in the TOP VIEW shown in FIG. 4. A carriage 45 is mounted on top of the bridge beam 43 and is powered using a carriage actuator 46 for providing translation in another direction which is orthogonal to the first direction. This second direction is depicted as the Y direction in the TOP VIEW shown in FIG. 4. Extending downward from the bridge beam 43 is a Z-mast 47, whose length is variable and is controlled using a Z-mast actuator 48. The Z-mast provides for translation in a third direction, orthogonal to the first two directions. This third direction is depicted as the Z direction in the SIDE VIEW shown in FIG. 4.

By providing movement in three orthogonal positions and delivering a laser beam throughout the system, the particular embodiment shown in FIG. 4 of a gantry positioning system provides for emitting the laser beam 11 at any location within the workspace of the test object 35 allows for performing ultrasonic testing using an ultrasonic testing system from a variety of field of view, similarly to the capability shown in FIG. 3. Also in similar fashion to FIG. 3, a laser beam conditioning system 37 may be used to provide for minimizing the divergence of the laser beam 11 as it exits the end of the Z-mast 47 of this particular embodiment of a gantry positioning system and is delivered to the test object 35. The laser beam conditioning system 37 could likewise be included within the optical transmission channels 22 of the gantry segments of the GPS to provide for conditioning and minimizing the divergence of the beam as it propagates through the GPS. If even more spatial control is desired for directing the laser beam 11 from the end of the Z-mast 47, a rotation attachment platform 49 may be attached to the end of the Z-mast allowing additional directional control and delivering of the laser beam 11 to the test object 35.

The present invention provides several benefits including a scaleable laser beam delivery system which is adaptable to gantry positioning systems (GPSs) of various sizes and weight by providing closed-loop error correction of the transmission of a laser beam provided by a remote laser source through a GPS. By performing scanning across the test object from multiple fields of view, the present invention provides for automated data acquisition of a test object for detecting material defects using ultrasonic techniques. Additionally, a laser beam conditioning system may be used to control various laser beam properties during transmission through the GPS and as the laser beam exits the GPS and travels toward the test object.

Although the present invention has been described in detail, it should be understood that various changes, substitutions and alterations can be made hereto without departing from the spirit and scope of the invention as described by the appended claims.

What is claimed is:

1. A gantry positioning and laser ultrasonic testing system with an integral laser beam delivery system, comprising:
   a gantry positioning system comprising a plurality of gantry members pivotally connected at each end and powered by a plurality of gantry actuators for positioning an end gantry member at any location within a predetermined volume wherein each gantry member comprises an optical transmission channel comprising at least two alignment fixtures and at least one position feedback sensor for providing an alignment signal;

an integral laser beam delivery system for delivering a laser beam emitted from a remote laser source to a test object first from a first field of view and subsequently from at least one additional field of view within said predetermined volume for acquiring test object data, comprising:

a remote laser source for emitting said laser beam, said laser beam being inserted into a first gantry member's optical transmission channel and exiting through an end gantry member's optical transmission channel;

a plurality of mirror actuators for controlling the angular alignment of a plurality of mirrors wherein at least one mirror being located at each pivotal connection of said gantry members in response to at least one of said alignment signals from said position feedback sensors for providing closed-loop error correction for unobstructed transmission of said laser beam through said optical transmission channels of said plurality of gantry members for directing said laser beam through said gantry positioning system; and a laser beam conditioning system for minimizing divergence of said laser beam; and an ultrasonic testing system for identifying material defects of said test object using said test object data.

2. The system of claim 1, wherein said plurality of mirrors comprise dual axis mirrors.

3. The system of claim 1, wherein said remote laser source comprises a $CO_2$ laser having a center wavelength of approximately 10.6 micro-meters.

4. The system of claim 1, wherein said test object comprises composite material.

5. The system of claim 1, wherein said plurality of mirror actuators provide at least 10 milli-radians positioning sensitivity of said plurality of mirrors.

6. The system of claim 1, further comprising an optical table for supporting said laser source wherein said optical table being attached to a vertical support column of said gantry positioning system.

7. The system of claim 1, further comprising:

an optical table for supporting said laser source wherein said optical table being attached to a vertical support column of said gantry positioning system; and a laser beam expander for inserting said laser beam into said first gantry member's optical transmission channel.

8. The system of claim 1, wherein said end gantry member comprises a rotation attachment platform.

9. The system of claim 1, wherein said laser beam conditioning system for minimizing divergence of said laser beam comprises an exit laser beam focusing system for focusing said laser beam onto said test object.

10. The system of claim 1, wherein said optical transmission channels of said plurality of gantry members comprise bellows-type enclosure for providing free space propagation of said laser beam and for providing air tight sealing for minimizing particulate contaminants within said optical transmission channels.

11. A gantry positioning and laser ultrasonic testing system with an integral laser beam delivery system, comprising:

a gantry positioning system, comprising:

a plurality of vertical support columns for supporting two runway beams;

a carriage mounted on a bridge beam spanning between said two runway beams comprising a carriage actuator for providing a first range of motion by translating said carriage across said bridge beam;

a bridge beam actuator for providing a second range of motion by translating said bridge beam along said two runway beams, said first and said second ranges of motion being orthogonal; and a Z-mast extending downward from said carriage assembly comprising an end gantry member and a Z-mast actuator for providing a third range of motion by adjusting the length of said Z-mast, said first, second, and third ranges of motion being orthogonal wherein said gantry positioning system positions said end gantry member at any location within a predetermined volume;

an integral laser beam delivery system comprising a plurality of enclosure segments pivotally interconnected at mirror assemblies for directing a laser beam emitted from a remote laser source along one of said vertical support columns, one of said two runway beams, said bridge beam, and said Z-mast and for directing said laser beam from said end gantry member at a test object from a first field of view and subsequently from at least one additional field of view within said predetermined volume for acquiring test object data, wherein;

each of said enclosure segments is enclosed for providing air tight sealing and comprise at least two alignment apertures and a position feedback sensor;

each mirror assembly comprises a mirror and a mirror actuator for controlling the alignment angle of said mirror in response to an alignment signal from said position feedback sensor for providing closed-loop error correction for unobstructed transmission of said laser beam through said optical transmission of said laser beam through said gantry positioning system; and a laser beam conditioning system for minimizing divergence of said laser beam; and a laser ultrasonic testing system for identifying material defects of said test object using said test object data.

12. A method for delivering a laser beam to a test object through a gantry positioning and laser ultrasonic testing system, comprising:

utilizing a gantry positioning system comprising a plurality of gantry members pivotally connected at each end and powered by a plurality of gantry actuators for positioning an end gantry member at any location within a predetermined volume wherein each gantry member comprises an optical transmission channel comprising at least two alignment fixtures and at least one position feedback sensor for providing an alignment signal for positioning an end gantry member at any location within a predetermined volume;

inserting a laser beam emitted from a remote laser source into a first gantry member's optical transmission channel;

controlling the angular alignment of a plurality of mirrors wherein at least one mirror being located at each pivotal connection of said gantry members in response to at least one alignment signal from a position feedback sensor for providing closed-loop error correction for unobstructed transmission of said laser beam through said optical transmission channels of said plurality of gantry members for directing said laser beam through said gantry positioning system;

directing said laser beam from an end gantry member at a test object first from a first field of view and subsequently from at least one additional field of view within said predetermined volume for acquiring test object data;

minimizing divergence of said laser beam using a laser beam conditioning system; and identifying material defects of said test object using a laser ultrasonic testing system using said test object data.

13. The method of claim 12, wherein said plurality of mirrors comprise dual axis mirrors.

14. The method of claim 12, wherein said remote laser source comprises a $CO_2$ laser having a center wavelength of approximately 10.6 micro-meters.

15. The method of claim 12, wherein said test object comprises composite material.

16. The method of claim 12, wherein controlling the angular alignment of a plurality of mirrors comprises providing at least 10 milli-radians positioning sensitivity of said plurality of mirrors.

17. The method of claim 12, further comprising supporting said laser source using an optical table wherein said optical table being attached to a vertical support column of said gantry positioning system.

18. The method of claim 12, further comprising:

supporting said laser source using an optical table wherein said optical table being attached to a vertical support column of said gantry positioning system, and inserting said laser beam into said first gantry member's optical transmission channel using a laser beam expander.

19. The method of claim 12, wherein said end gantry member comprises a rotation attachment platform and said laser beam conditioning system for minimizing divergence of said laser beam comprises an exit laser beam focusing system for focusing said laser beam onto said test object.

20. The method of claim 12, wherein said optical transmission channels of said plurality of gantry members comprise bellows-type enclosure for providing free space propagation of said laser beam and for providing air tight sealing for minimizing particulate contaminants within said optical transmission channels.

* * * * *